(12) United States Patent
Kidwell, Jr. et al.

(10) Patent No.: US 10,770,646 B2
(45) Date of Patent: Sep. 8, 2020

(54) MANUFACTURING METHOD FOR FLEXIBLE PMUT ARRAY

(71) Applicant: QUALCOMM Incorporated, San Diego, CA (US)

(72) Inventors: Donald William Kidwell, Jr., Los Gatos, CA (US); Ravindra Shenoy, Dublin, CA (US); Jon Lasiter, Stockton, CA (US)

(73) Assignee: QUALCOMM Incorporated, San Diego, CA (US)

( * ) Notice: Subject to any disclaimer, the term of this patent is extended or adjusted under 35 U.S.C. 154(b) by 417 days.

(21) Appl. No.: 15/443,330

(22) Filed: Feb. 27, 2017

(65) Prior Publication Data
US 2017/0252777 A1 Sep. 7, 2017

Related U.S. Application Data

(60) Provisional application No. 62/302,072, filed on Mar. 1, 2016.

(51) Int. Cl.
*H01L 41/22* (2013.01)
*H01L 41/047* (2006.01)
(Continued)

(52) U.S. Cl.
CPC ............ *H01L 41/22* (2013.01); *A61B 8/4483* (2013.01); *H01L 27/20* (2013.01);
(Continued)

(58) Field of Classification Search
CPC ............ H01L 41/0472; H01L 41/0475; H01L 41/0536; H01L 41/0815; H01L 41/0973; H01L 41/29; H01L 41/33; H01L 41/314; H01L 27/20; H01L 41/22; Y10T 29/42; B06B 1/0622; A61B 8/4483
See application file for complete search history.

(56) References Cited

U.S. PATENT DOCUMENTS

2015/0158052 A1* 6/2015 Latev .................... H01L 41/29
310/316.01
2015/0200350 A1 7/2015 Hajati et al.

FOREIGN PATENT DOCUMENTS

EP 1453103 A2 9/2004
JP 2002354589 A * 12/2002
WO 2016007250 A1 1/2016

OTHER PUBLICATIONS

International Search Report and Written Opinion—PCT/US2017/019916—ISA/EPO—dated Jun. 12, 2017.

* cited by examiner

*Primary Examiner* — A. Dexter Tugbang
(74) *Attorney, Agent, or Firm* — Paradice and Li LLP

(57) ABSTRACT

Techniques and structures are provided for manufacturing a flexible PMUT array. In one embodiment, a piezoelectric micromechanical ultrasonic transducer (PMUTs) array comprises a plurality of PMUTs, where each PMUT in the flexible array of PMUTs includes: a first polymer layer configured to support the PMUT, a mechanical layer configured to provide planarization to the PMUT, a first electrode, a second electrode, a piezoelectric layer configured to separate the first electrode and the second electrode, patterns on the first electrode, the piezoelectric material, and the second electrode configured to route electrical signals, and a cavity configured to adjust a frequency response of the PMUT.

12 Claims, 19 Drawing Sheets

(51) Int. Cl.
*A61B 8/00* (2006.01)
*H01L 41/09* (2006.01)
*H01L 27/20* (2006.01)
*H01L 41/053* (2006.01)
*H01L 41/08* (2006.01)
*H01L 41/29* (2013.01)
*H01L 41/314* (2013.01)
*H01L 41/33* (2013.01)
*B06B 1/06* (2006.01)

(52) U.S. Cl.
CPC ...... *H01L 41/0472* (2013.01); *H01L 41/0475* (2013.01); *H01L 41/0536* (2013.01); *H01L 41/0815* (2013.01); *H01L 41/0973* (2013.01); *H01L 41/29* (2013.01); *H01L 41/314* (2013.01); *H01L 41/33* (2013.01); *B06B 1/0622* (2013.01); *Y10T 29/42* (2015.01)

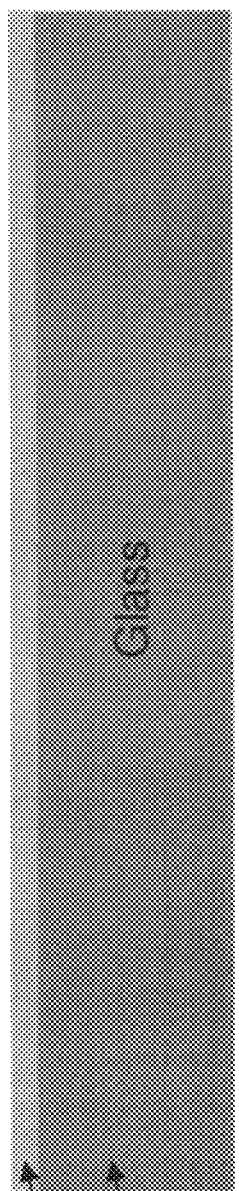
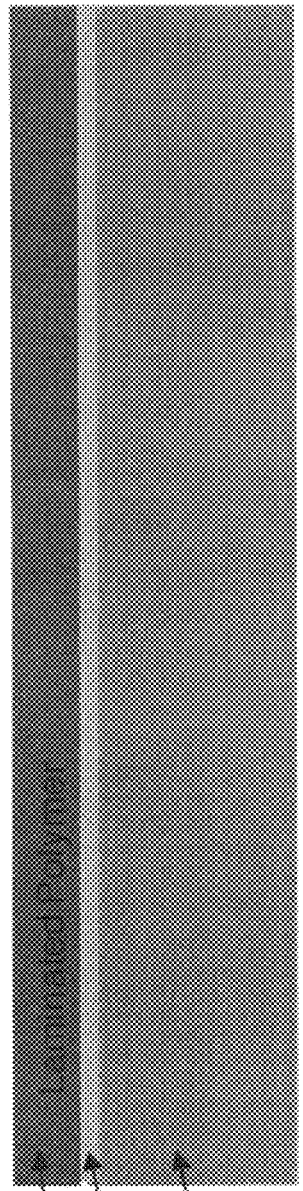
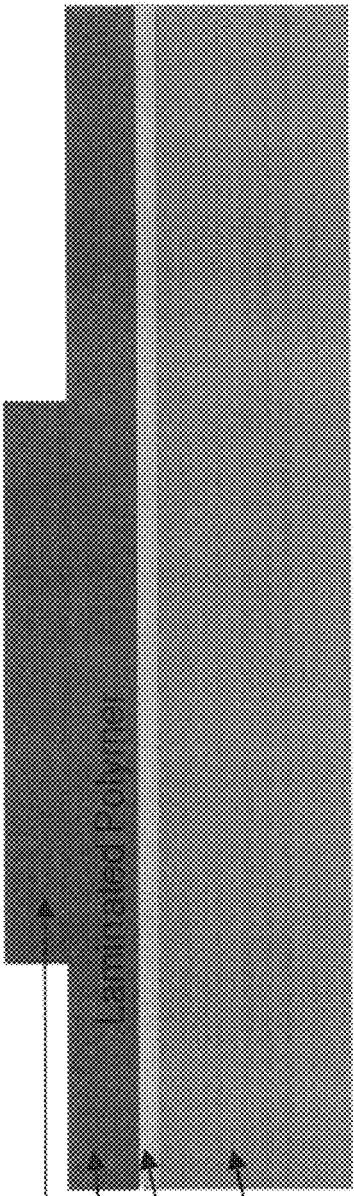

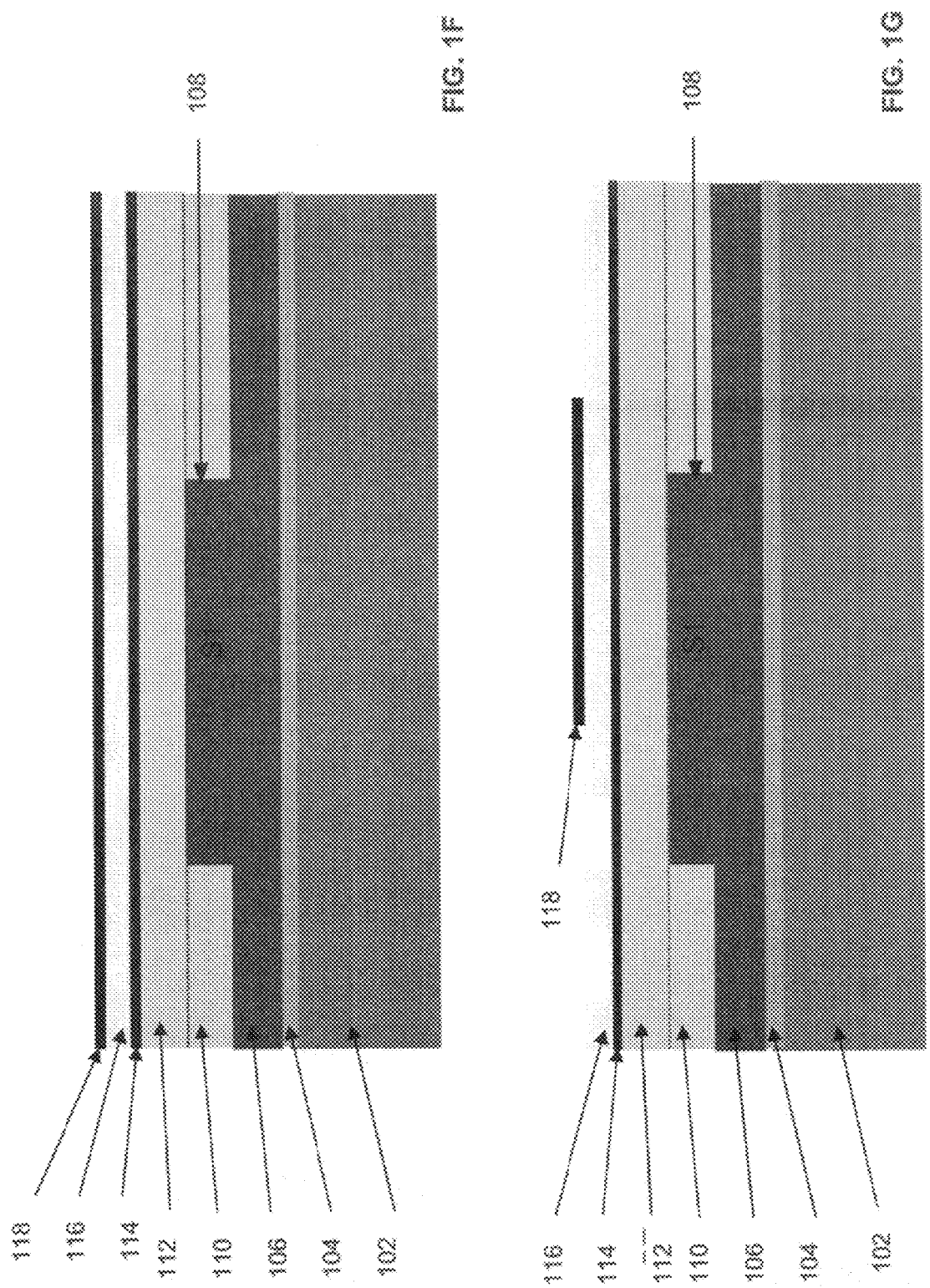

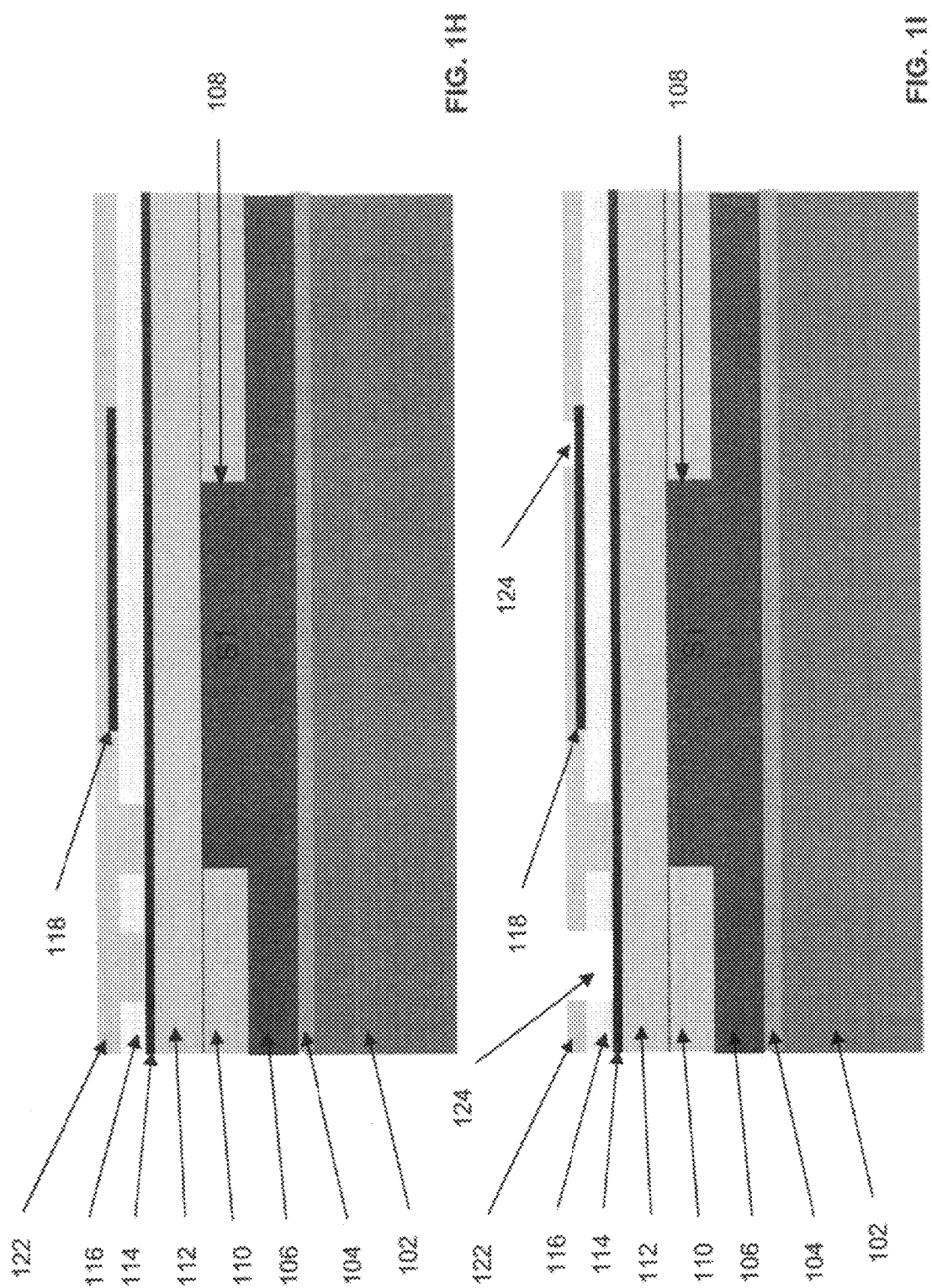

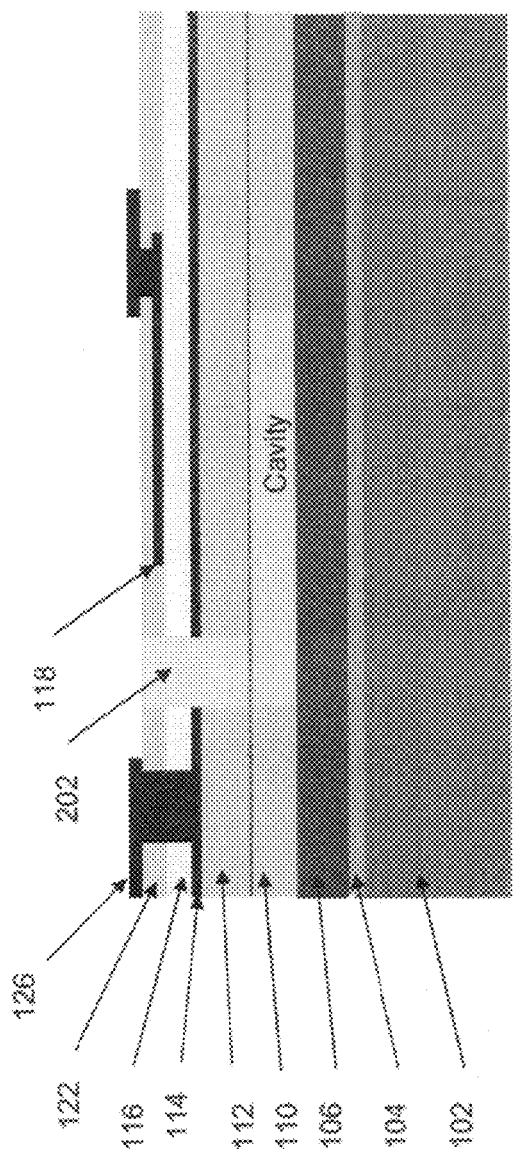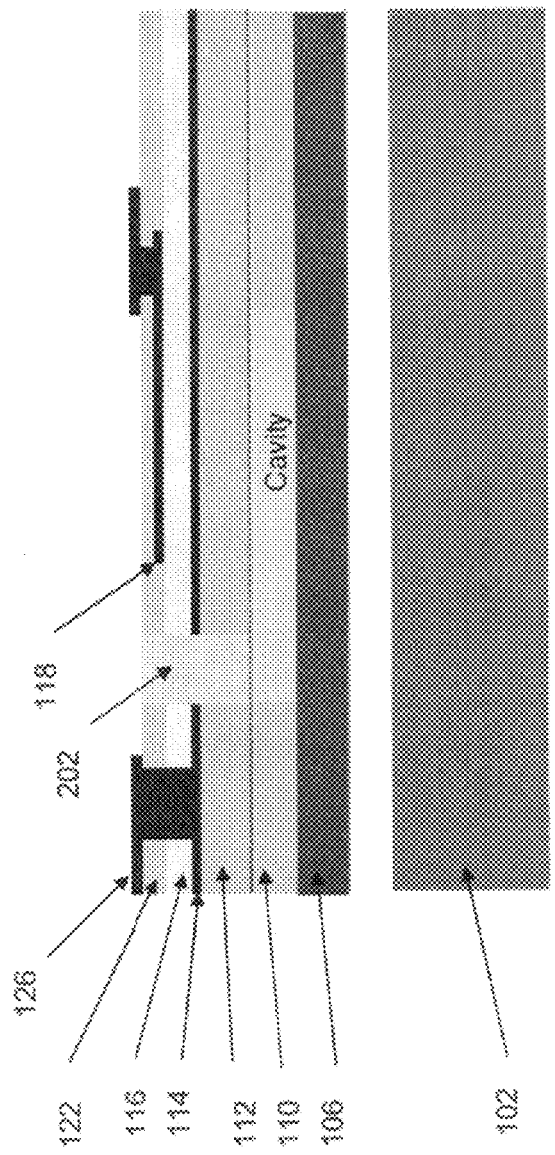

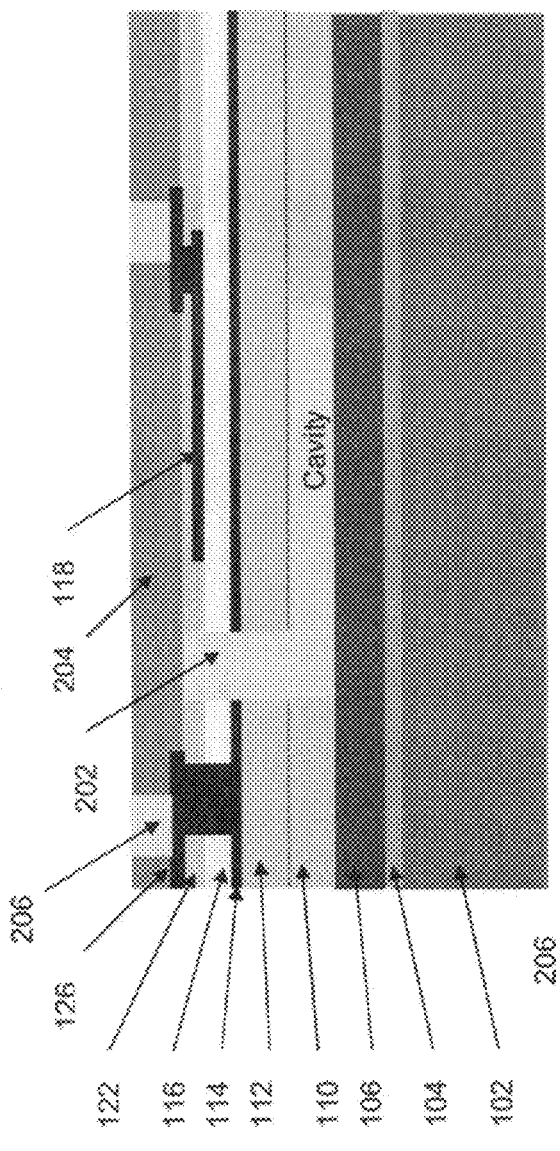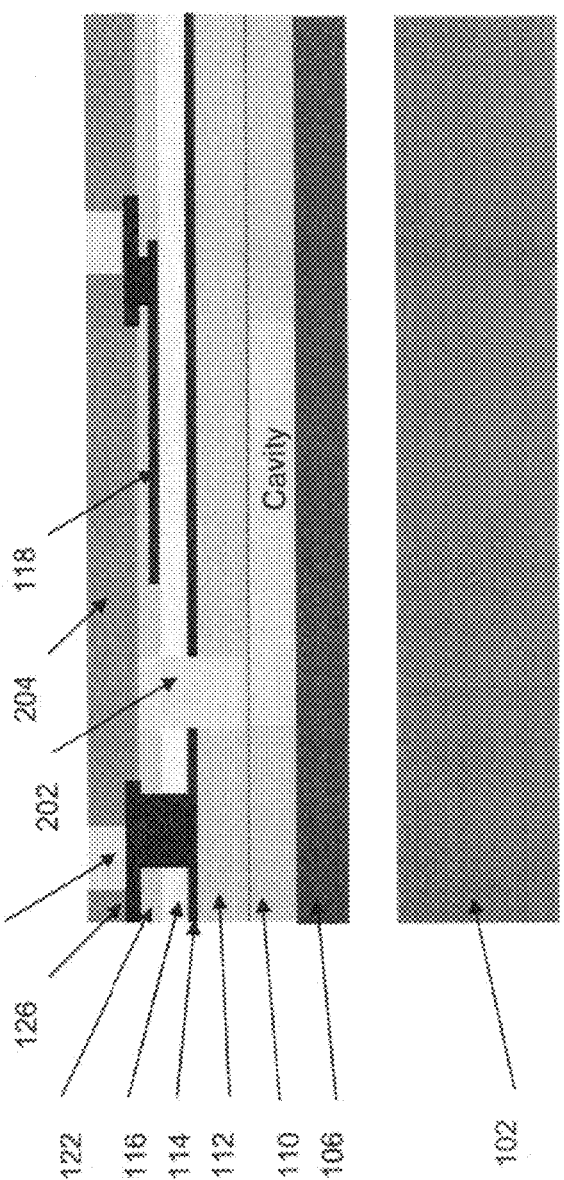

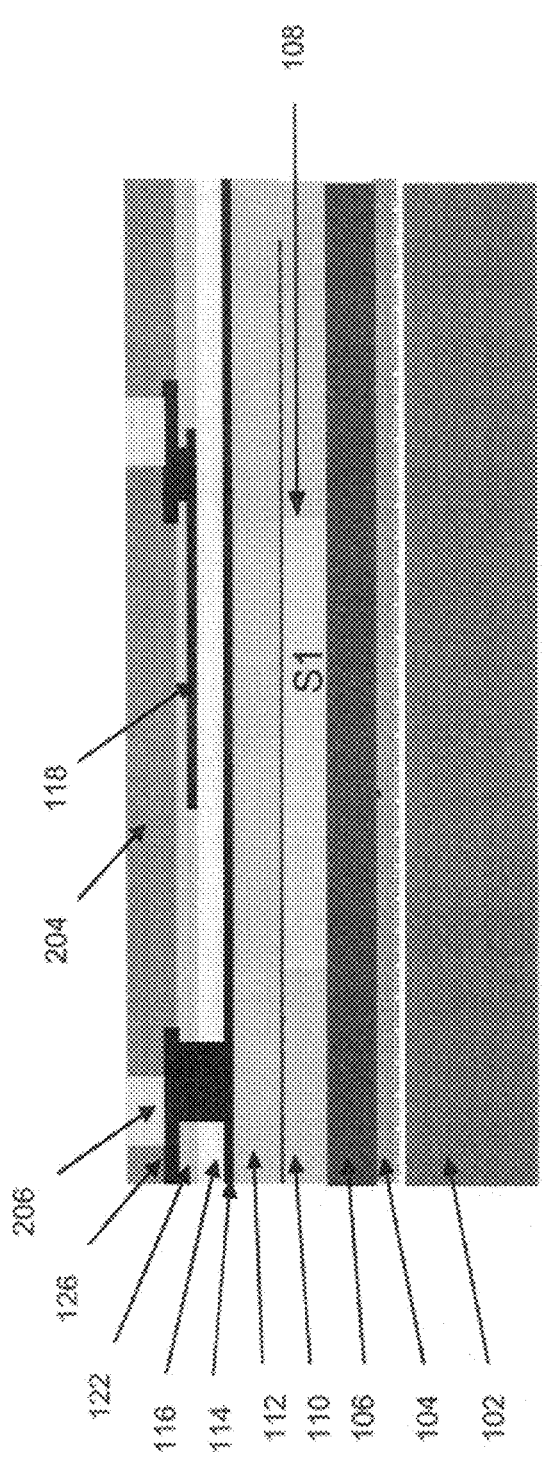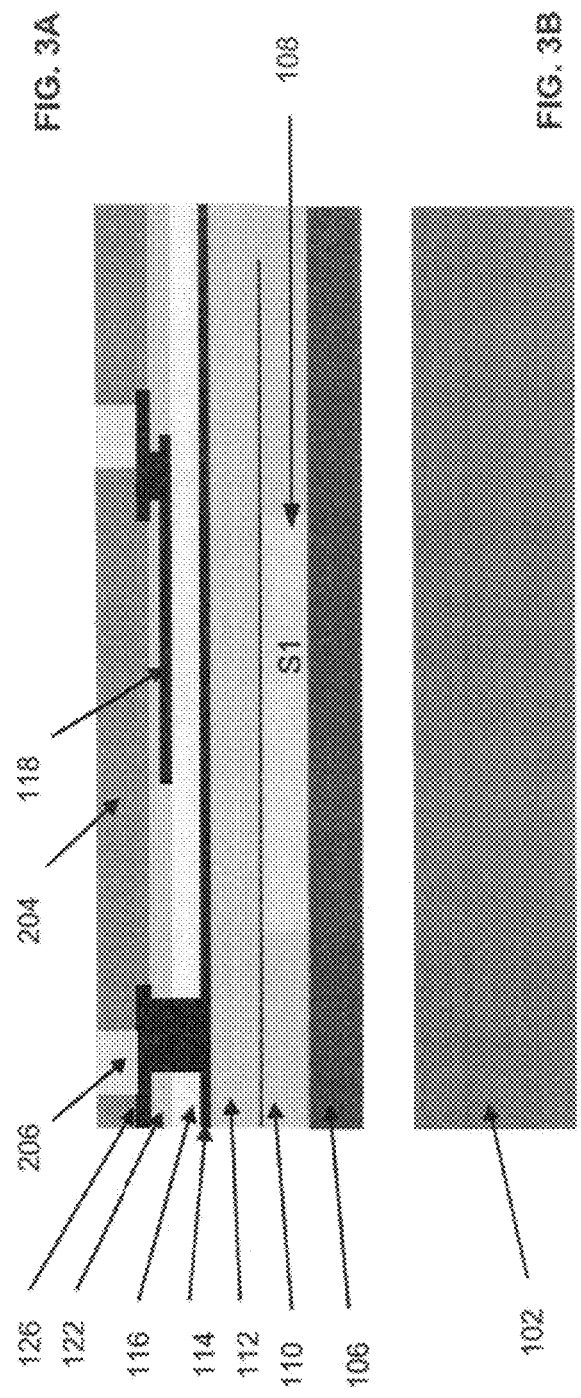

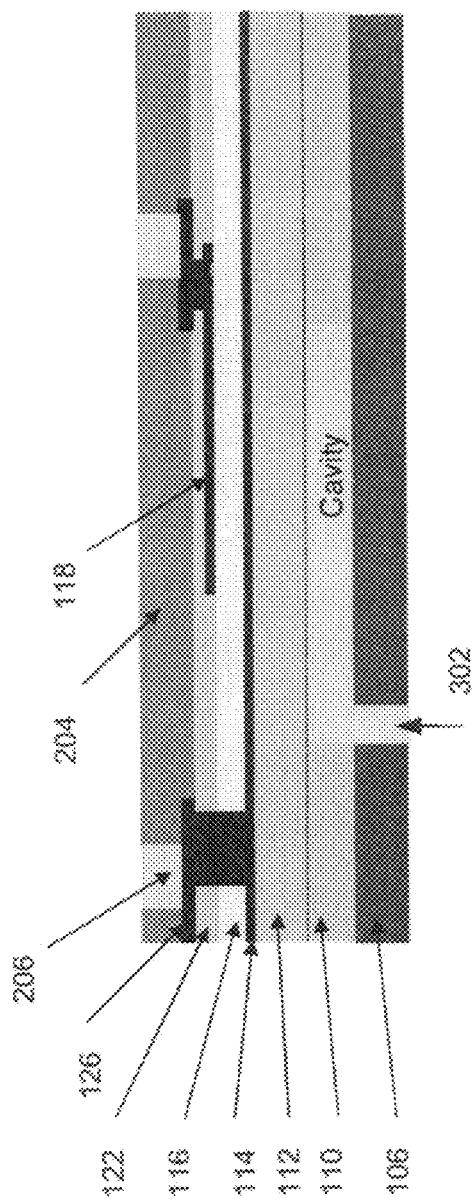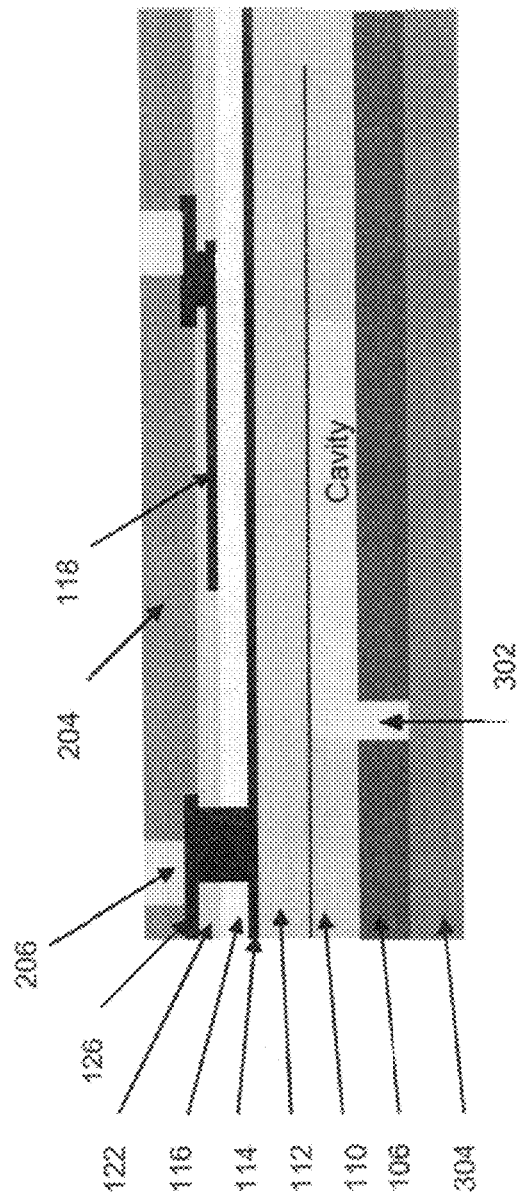

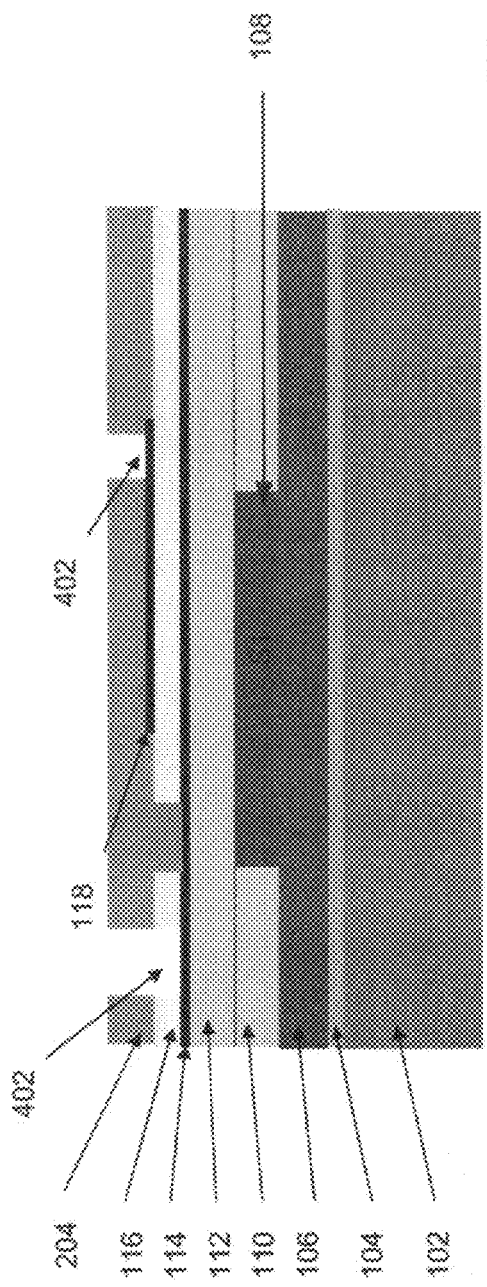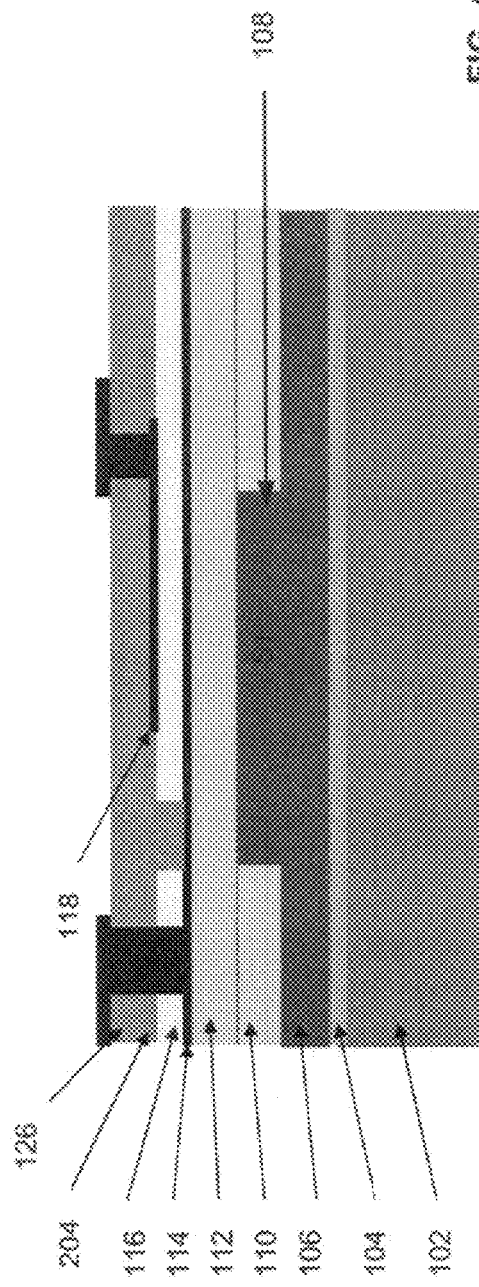

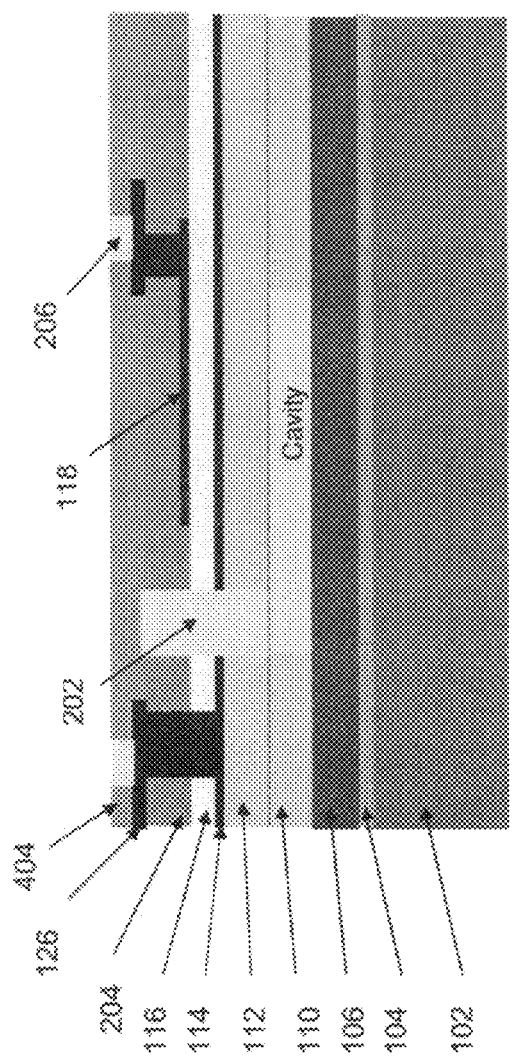
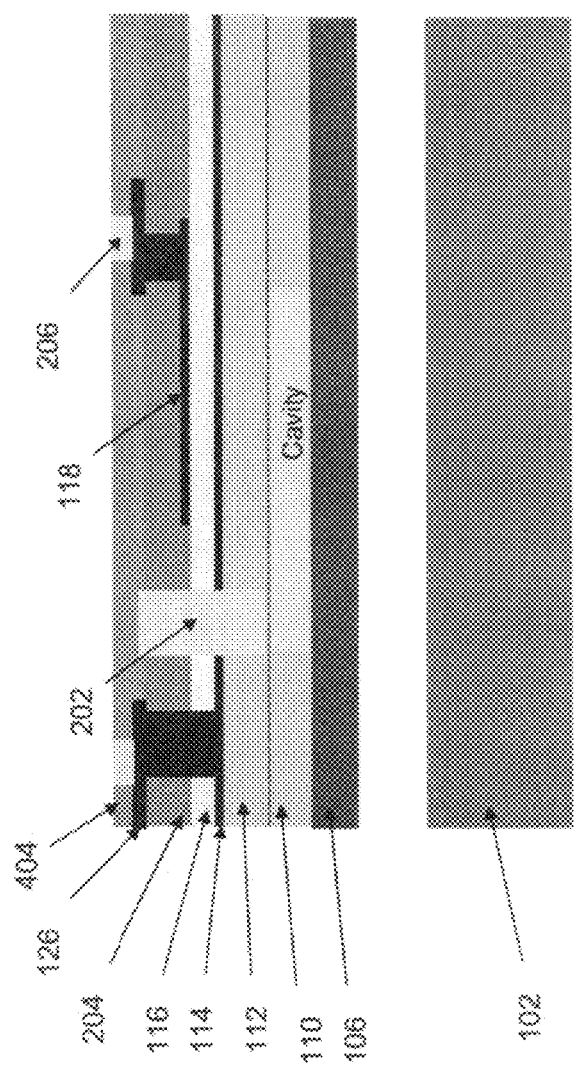
FIG. 4E
FIG. 4F

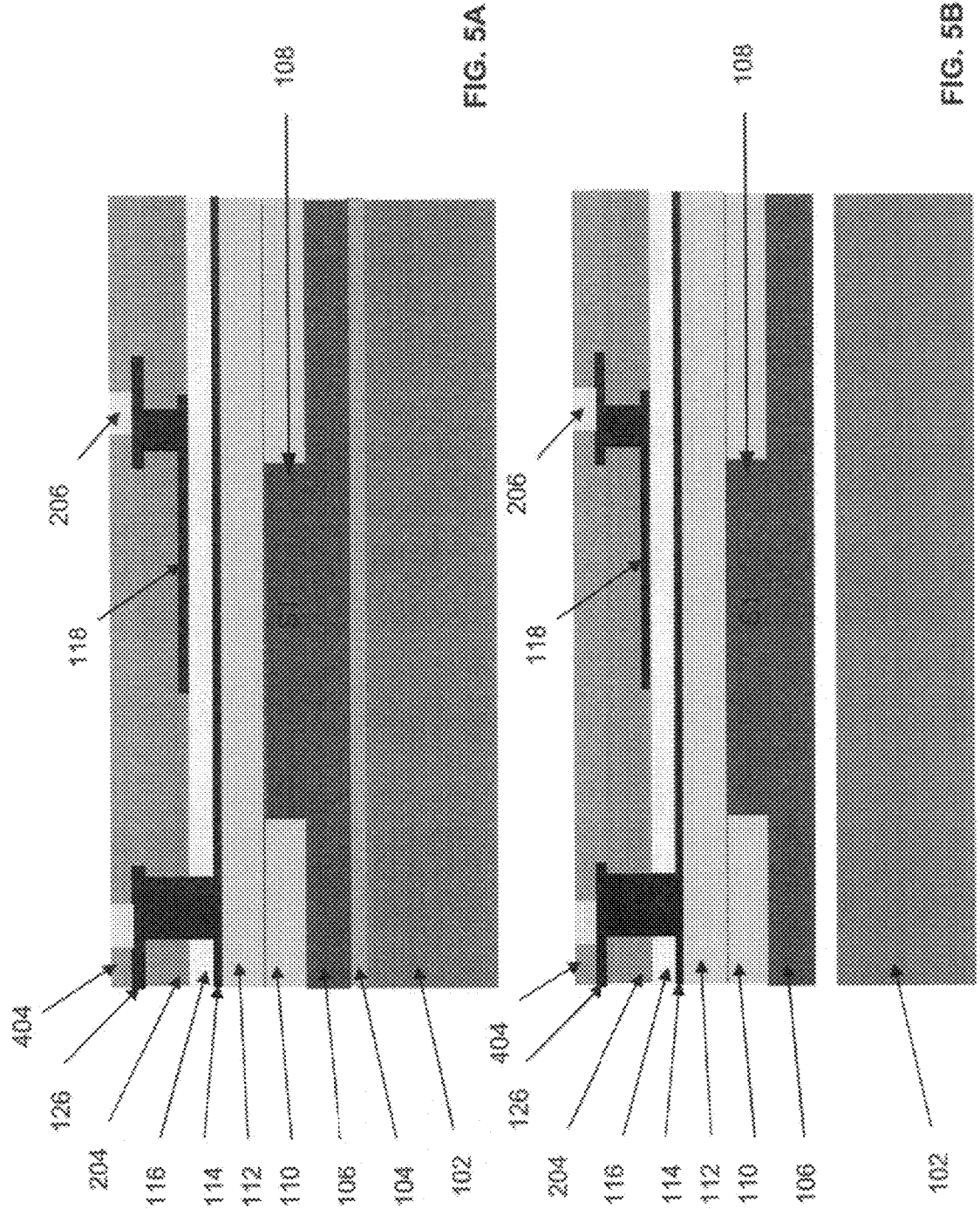

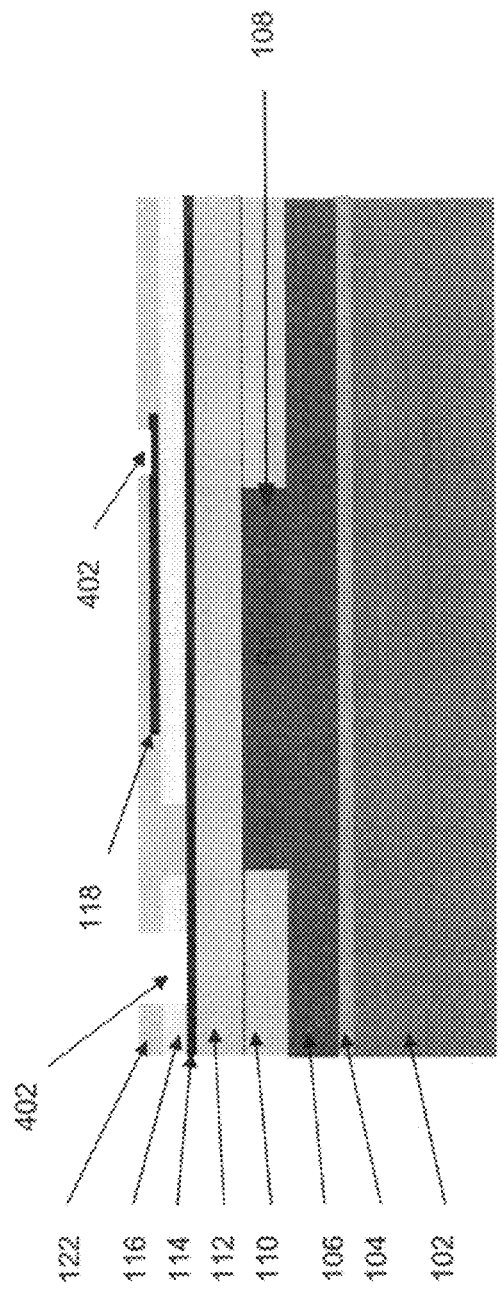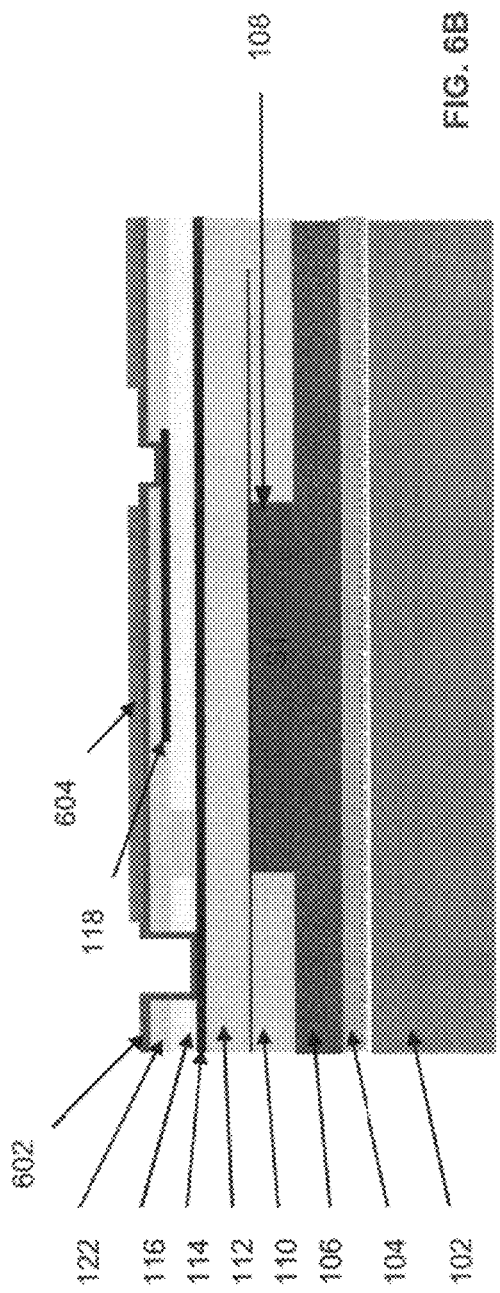

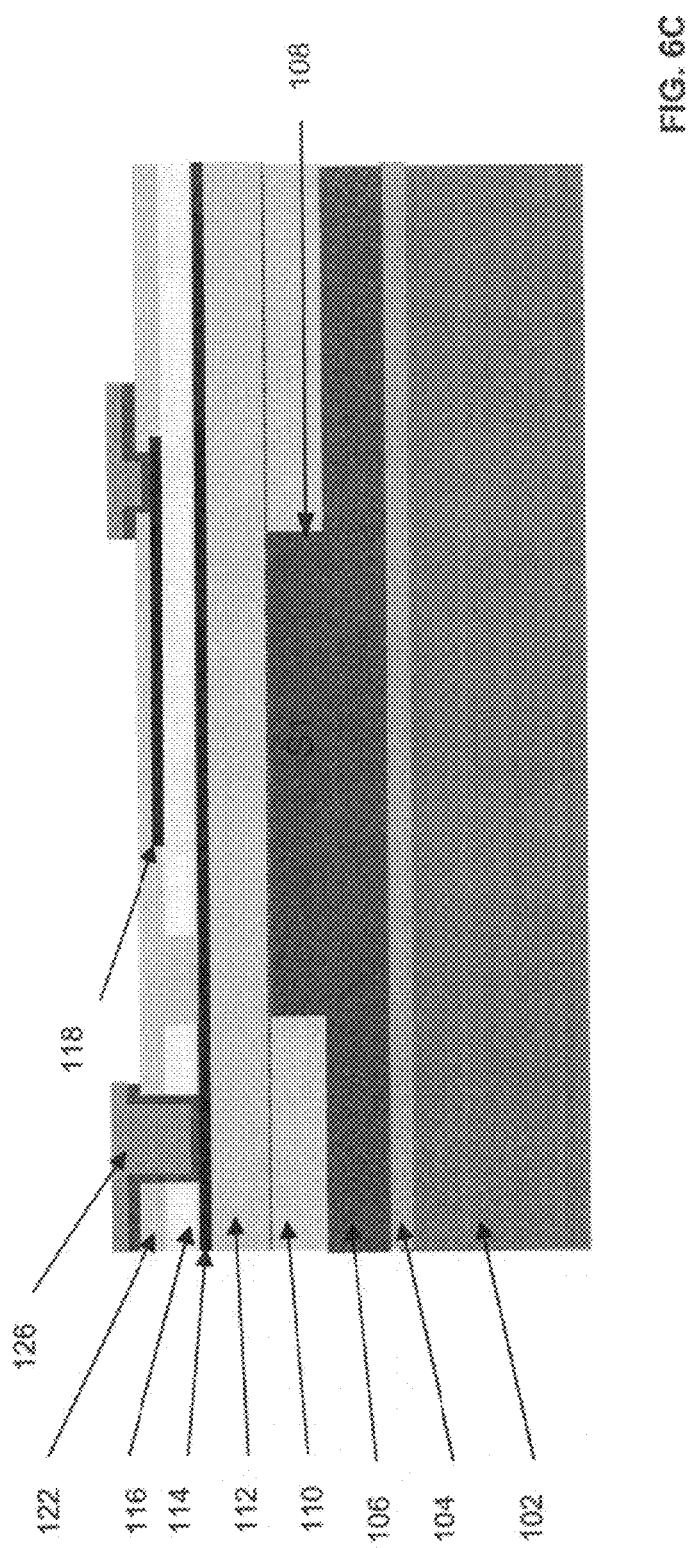

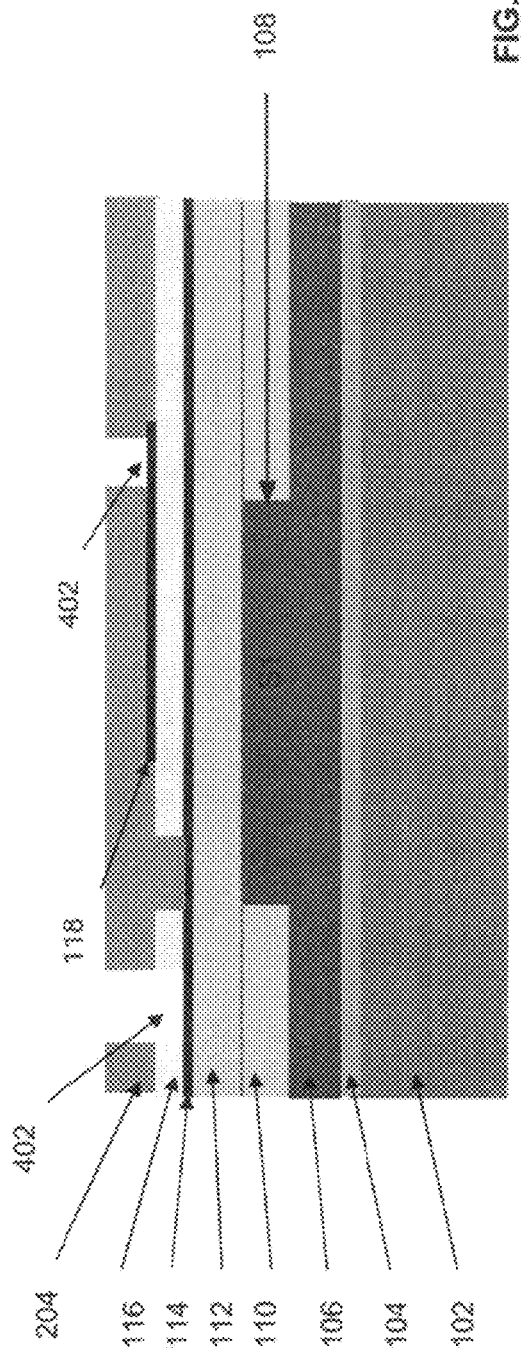
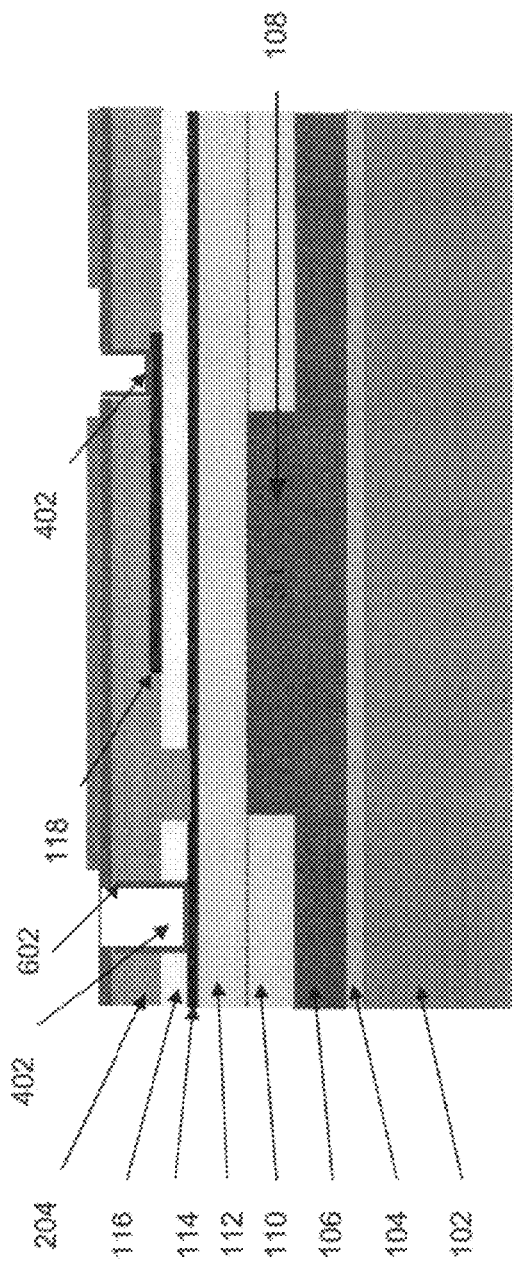
FIG. 7A
FIG. 7B

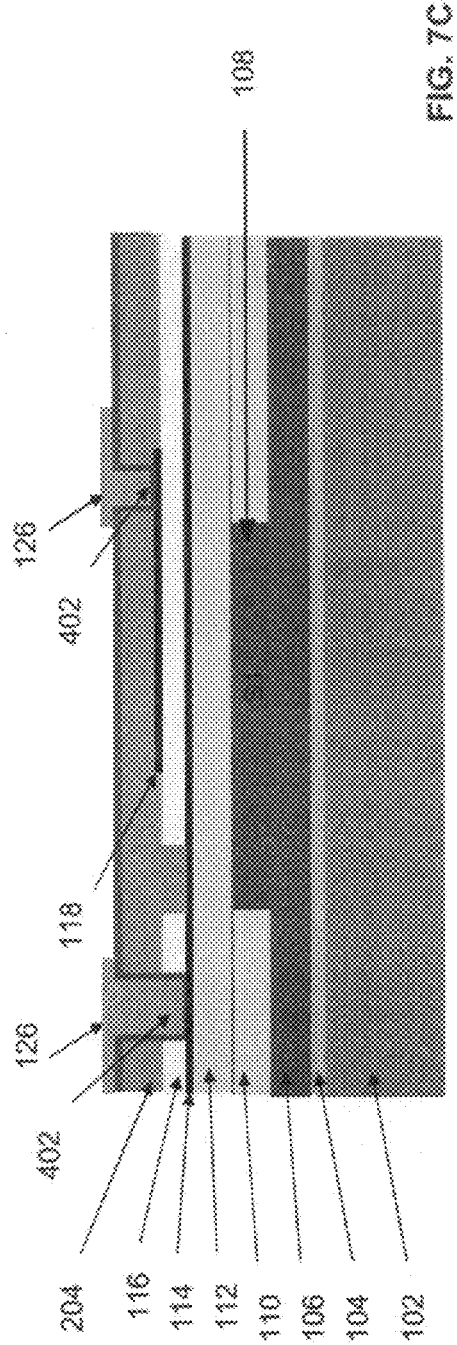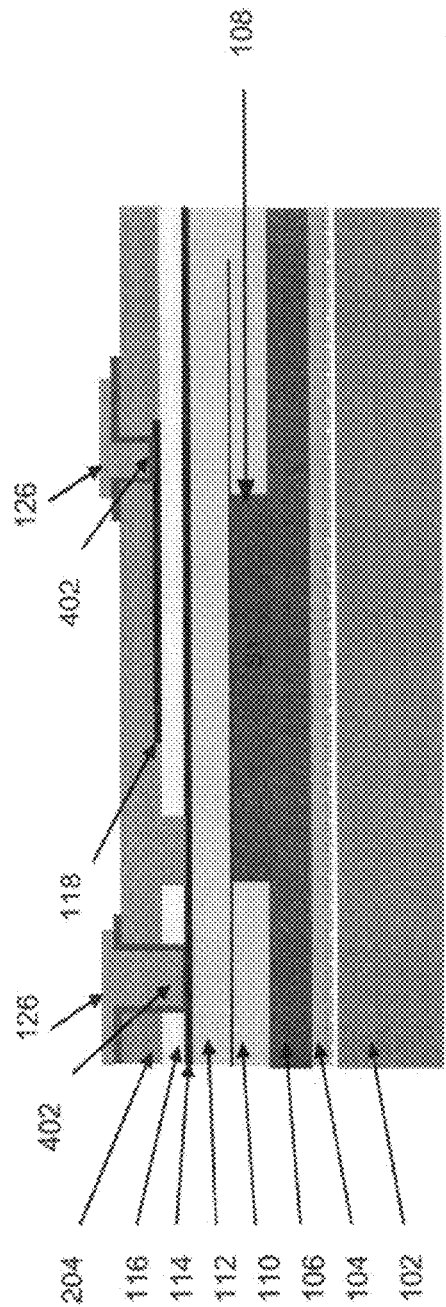

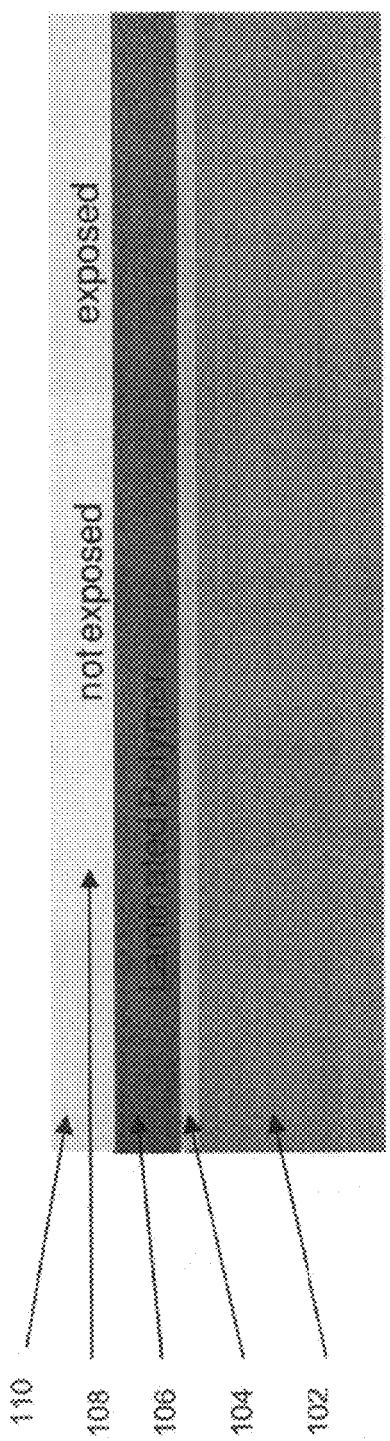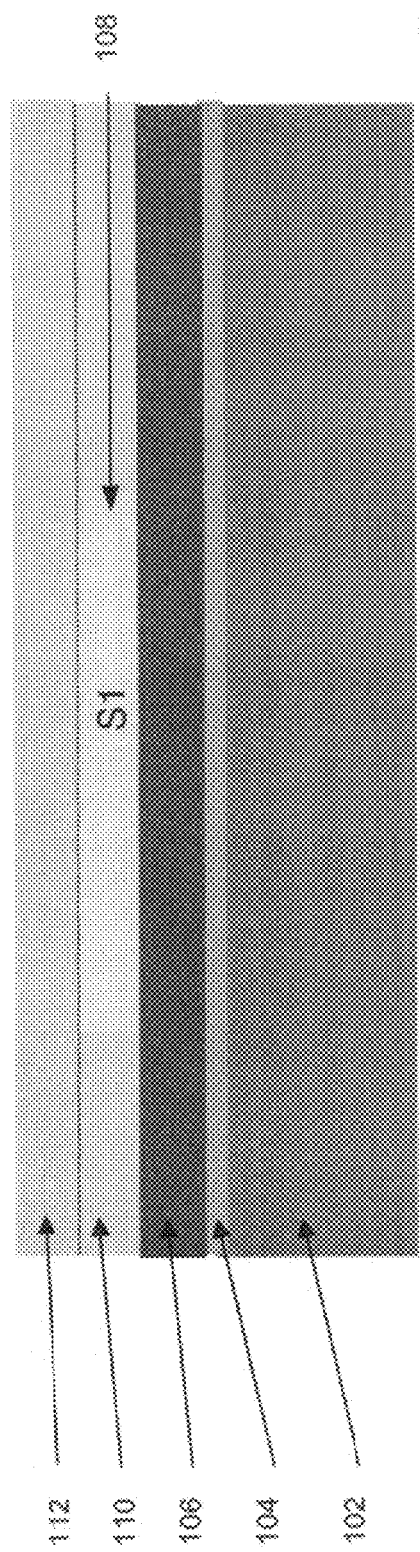

MANUFACTURING METHOD FOR FLEXIBLE PMUT ARRAY

CROSS REFERENCE TO RELATED APPLICATION

This application claims the benefit of U.S. provisional patent application No. 62/302,072, "Flexible PMUT Array," filed Mar. 1, 2016, which is assigned to the assignee hereof. The aforementioned United States provisional patent application is hereby incorporated by reference in its entirety.

FIELD

The present disclosure relates to the field of ultrasonic sensors. In particular, the present disclosure relates to embodiments of a flexible piezoelectric micromechanical ultrasonic transducer (PMUT) array and methods for manufacturing the same.

BACKGROUND

Some conventional ultrasonic transducer devices, such as the devices described in U.S. Pat. 5,744,898 and U.S. Pat. 8,596,140 B2, tend to be rigid and large in size. These devices are not suited to be adopted as an implantable or ingestible device for non-invasive imaging applications. In some recently improved ultrasound diagnostic imaging devices, such as the devices described in U.S. Patent Application 2014/0276079 A1, a tube/wire is required along with the ultrasound transducers to be inserted into a patient. These devices are also unsuitable to be adopted as an implantable or ingestible device for non-invasive imaging applications. Some other ultrasonic transducer devices, such as the devices described in US Patent Application 2011/0130658 A1 and U.S. Pat. No. 8,647,328 B2, are concerned with using the devices, but fail to address the apparatuses and methods for making such devices small with a plurality of flexible ultrasonic transducers such that these components may be packaged into a sensor device for implantable or ingestible or other non-invasive applications. Therefore, there is a need for a flexible piezoelectric micromechanical ultrasonic transducer array that may be adopted as an implantable or ingestible or other non-invasive applications, and methods for manufacturing the same.

SUMMARY

Embodiments of a flexible PMUT array and methods for manufacturing the same are disclosed. In one embodiment, a method of forming a flexible array of piezoelectric micromechanical ultrasonic transducers (PMUTs), includes providing a carrier configured to support the flexible array of PMUTs, providing a release layer configured to adhere the flexible array of PMUTs to the carrier, forming the flexible array of PMUTs over the release layer, and removing the release layer to separate the flexible array of PMUTs from the carrier.

The method of forming the flexible array of PMUTs includes, for each PMUT in the flexible array of PMUTs: laminating a first polymer layer configured to support the PMUT, depositing a sacrificial material configured to pattern a cavity of the PMUT, depositing a planarization layer to provide a smooth, level surface for subsequent layers and forming the side walls of the cavity, depositing a mechanical layer configured to provide planarization to the PMUT and one horizontal wall of the cavity, depositing a first electrode, depositing a piezoelectric layer configured to separate the first electrode and a second electrode, depositing the second electrode, and creating patterns on the first electrode, the piezoelectric material, and the second electrode configured to route control signals of the PMUT. According to aspects of the present disclosure, the mechanical layer may include a planarization layer configured to provide chemical mechanical planarization to the PMUT, a mechanical membrane configured to provide stiffness to the PMUT and frequency response adjustment, or some combination thereof.

The method may further include depositing a passivation layer configured to encapsulate the first electrode, the piezoelectric layer and the second electrode, etching contact vias configured to access the first electrode and the second electrode, and depositing pads and/or a redistribution layer configured to route electrical signals to the first electrode and the second electrode.

In some implementations, the method may further include forming a cavity configured to adjust a frequency response of the PMUT, laminating a second polymer layer configured to encapsulate the first electrode, the piezoelectric layer and the second electrode, and forming pattern vias configured to support signal access through the redistribution layer.

In some other implementations, the method may further include laminating a second polymer layer configured to encapsulate the first electrode, the piezoelectric layer and the second electrode, forming pattern vias configured to support signal access through the redistribution layer, separating the PMUT from the carrier, drilling a release via in the first polymer layer, forming a cavity configured to adjust a frequency response of the PMUT by removing the sacrificial material using the release via, and laminating a fourth polymer layer configured to enclose the cavity.

In yet some other implementations, the method may further include laminating a second polymer layer configured to encapsulate the first electrode, the piezoelectric layer and the second electrode, patterning contact vias configured to access the first electrode and the second electrode, and depositing pads and/or a redistribution layer configured to route electrical signals to the first electrode and the second electrode, and forming a cavity configured to adjust a frequency response of the PMUT.

In yet some other implementations, the method may further include laminating a third polymer layer configured to protect the PMUT, forming pattern vias configured to support signal access through the redistribution layer, separating the PMUT from the carrier, drilling a release via in the first polymer layer, forming a cavity configured to adjust a frequency response of the PMUT by removing the sacrificial material using the release via, and laminating a fourth polymer layer configured to enclose the cavity.

In another embodiment, a flexible array PMUTs may comprise a plurality of PMUTs, where each PMUT in the flexible array of PMUTs includes: a first polymer layer configured to support the PMUT, a mechanical layer configured to provide planarization to the PMUT, a first electrode, a second electrode, a piezoelectric layer configured to separate the first electrode and the second electrode, patterns on the first electrode, the piezoelectric material, and the second electrode configured to route electrical signals, and a cavity configured to adjust a frequency response of the PMUT. Note that the mechanical layer may include a planarization layer configured to provide chemical mechanical planarization to the PMUT, a mechanical membrane configured to provide stiffness to the PMUT as well as frequency response adjustment, or some combination thereof.

The flexible array of PMUTs may further include a passivation layer configured to encapsulate the first electrode, the piezoelectric layer and the second electrode, contact vias configured to access the first electrode and the second electrode, and pads and/or a redistribution layer configured to route the electrical signals to the first electrode and the second electrode.

The flexible array of PMUTs may further include a second polymer layer configured to encapsulate the first electrode, the piezoelectric layer and the second electrode, and pattern vias configured to support signal access through the redistribution layer. The flexible array of PMUTs may further include a release via through the first polymer layer. The flexible array of PMUTs may further include a fourth polymer layer configured to enclose the cavity.

In some implementations, the cavity may be oriented to have an opening through the piezoelectric layer, and it may be configured to control the PMUT to operate in a first range of frequency response.

In some other implementations, the cavity may be oriented to have an opening through the first polymer layer, and it may be configured to control the PMUT to operate in a second range of frequency response.

In yet some other implementations, the cavity may be enclosed in one or more substrates of the PMUT, and it may encapsulate a gaseous medium and may be configured to control the PMUT to operate in a third range of frequency response.

In yet some other implementations, the cavity may be enclosed in one or more substrates of the PMUT, and it may encapsulate a vacuum and may be configured to control the PMUT to operate in a fourth range of frequency response.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. The drawings are shown for illustration purposes and they are not drawn to scale. Like numbers are used throughout the figures.

FIGS. 1A-1J illustrate exemplary methods for forming a flexible PMUT array according to aspects of the present disclosure.

FIGS. 2A-2D illustrate supplementary methods to the methods of FIGS. 1A-1J for forming a flexible PMUT array according to aspects of the present disclosure.

FIGS. 3A-3D illustrate supplementary methods to the methods of FIGS. 1A-1J for forming another flexible PMUT array according to aspects of the present disclosure.

FIGS. 4A-4F illustrate supplementary methods to the methods of FIGS. 1A-1J for forming yet another flexible PMUT array according to aspects of the present disclosure.

FIGS. 5A-5D illustrate supplementary methods to the methods of FIGS. 1A-1J for forming yet another flexible PMUT array according to aspects of the present disclosure.

FIGS. 6A-6C illustrate an exemplary implementation for forming a redistribution layer according to aspects of the present disclosure.

FIGS. 7A-7D illustrate another exemplary implementation for forming a redistribution layer according to aspects of the present disclosure.

FIGS. 8A-8B illustrate an exemplary implementation for forming a cavity in a PMUT according to aspects of the present disclosure.

DESCRIPTION OF EMBODIMENTS

Figure 1D:
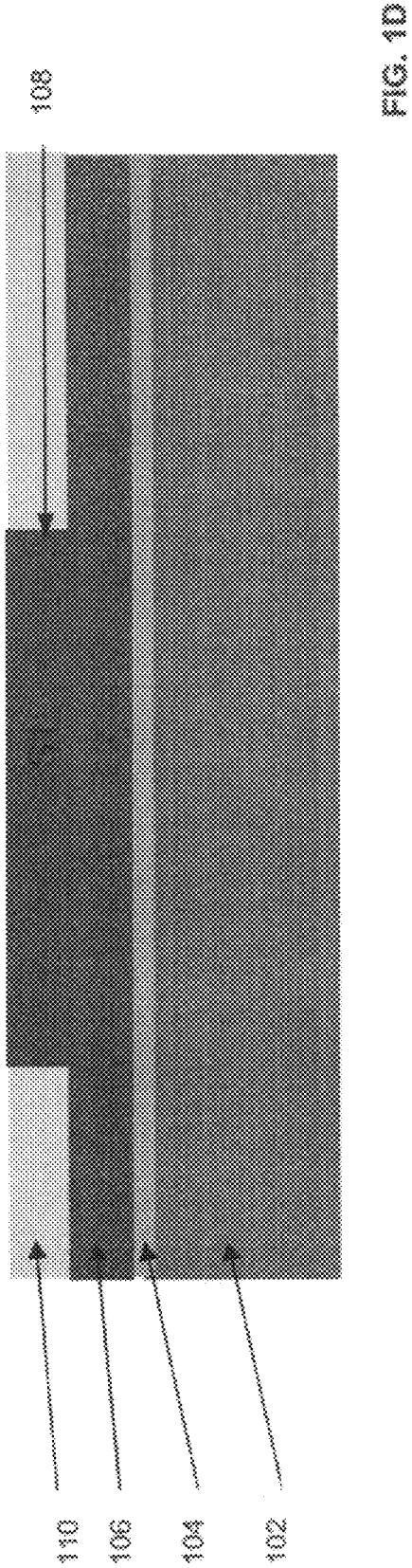

Embodiments of a flexible PMUT array and methods for manufacturing the same are disclosed. The following descriptions are presented to enable any person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

According to aspects of the present disclosure, the flexible PMUT array described herein may be adapted to be an implantable or ingestible device for non-invasive applications, for example detailed imaging. The flexible PMUT array may also be adapted to be a part of wearable devices, such as wrist bands, rings and patches, for monitoring and therapeutic applications. The flexible PMUT array may further be adapted to be an endoscope. In some implementations, the flexible PMUT array may be fabricated using existing wafer tools, as well as flexible polymer processing techniques such as lamination, spin-on or doctor blade coating. In some implementations, since the carrier may be temporary and can be removed, the cavity of the PMUT may be formed through a via at the front side or the back side of the PMUT.

According to aspects of the present disclosure, the following table provides names, their corresponding brief descriptions and exemplary materials that may be used for the various layers of a PMUT as described in FIGS. 1A-1J to FIG. 8A-8B. The contents of the table show certain particular implementations. Different implementations, such as M1 may be used as an electrode for signal while M2 may be used as an electrode for circuit ground may be implemented. In addition, different materials may be used to construct the different layers of the PMUT, in addition to the materials shown in the table.

| Layer Name | Description | Exemplary Material(s) |
| --- | --- | --- |
| SUB | Rigid substrate | Glass, Silicon |
| CAR | Carrier substrate | Glass, Silicon, PCB core |
| REL | Release layer for carrier | UV release adhesive |
| PL1 | Base planarization layer | Oxide (e.g., polished/plasma etched) |
| PT | Platen/mechanical membrane | Oxide |
| ENC | Encapsulation/passivation | Oxide |
| SEn | Laminated polymer layer | Photo-imagable polymer |
| M1 | Bottom electrode (Ground plane) | Moly |
| M2 | Top electrode (Signal) | Moly/Aluminum |
| M3 | Routing/pads | Aluminum (or plated Cu) |
| A2 | Piezoelectric material | Aluminum Nitride (200 deg. C.) |

-continued

| Layer Name | Description | Exemplary Material(s) |
|---|---|---|
| V1 | Membrane release via | Via to allow release of membrane cavity |
| V2 | Electrode contact vias | Contact vias for M1/M2 electrodes |
| VP | Pad vias | Via to open passivation for contact to M3 |
| S1 | Cavity release layer | a-Si (or Mo/polymer) |
| E1 | Encapsulation layer | |

FIGS. 1A-1J illustrate exemplary methods for forming a flexible PMUT array according to aspects of the present disclosure. FIG. 1A illustrates an example of coating a glass or silicon carrier (labeled as 102 and also referred to as CAR) with a release film (labeled as 104 and also referred to as REL). FIG. 1B illustrates an example of laminating a photo definable polymer (labeled as 106 and also referred to as SE1) on top of the release film. FIG. 1C illustrates an example of depositing a sacrificial material (labeled as 108 and also referred to as S1), which can be patterned and etched to define a cavity of the PMUT.

Figure 1E:
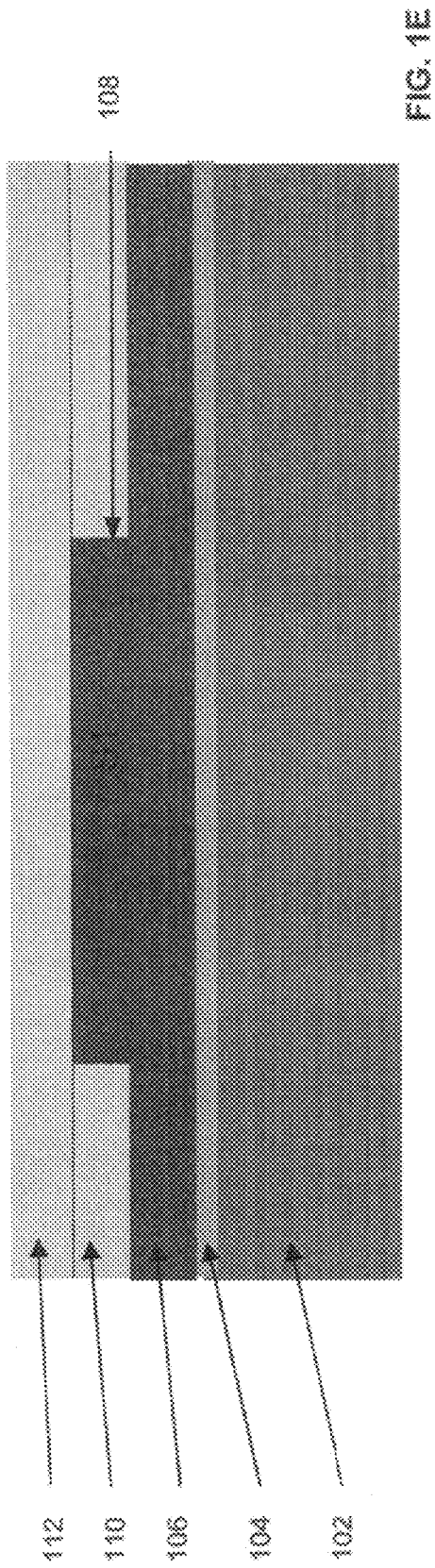

FIG. 1D illustrates an example of depositing an oxide layer (labeled as 110 and also referred to as PL1) and performing planarization using chemical-mechanical planarization or etch-back. FIG. 1E illustrates an example of depositing an oxide mechanical layer (labeled as 112 and also referred to as PT).

FIG. 1F illustrates an example of depositing a piezoelectric stack, including a bottom electrode (labeled as 114 and also referred to as M1), a piezoelectric material (labeled as 116 and also referred to as A2), and a top electrode (labeled as 118 and also referred to as M2). FIG. 1G illustrates an example of forming patterns on M1 114, M2 118, and A2 116.

Figure 1J:
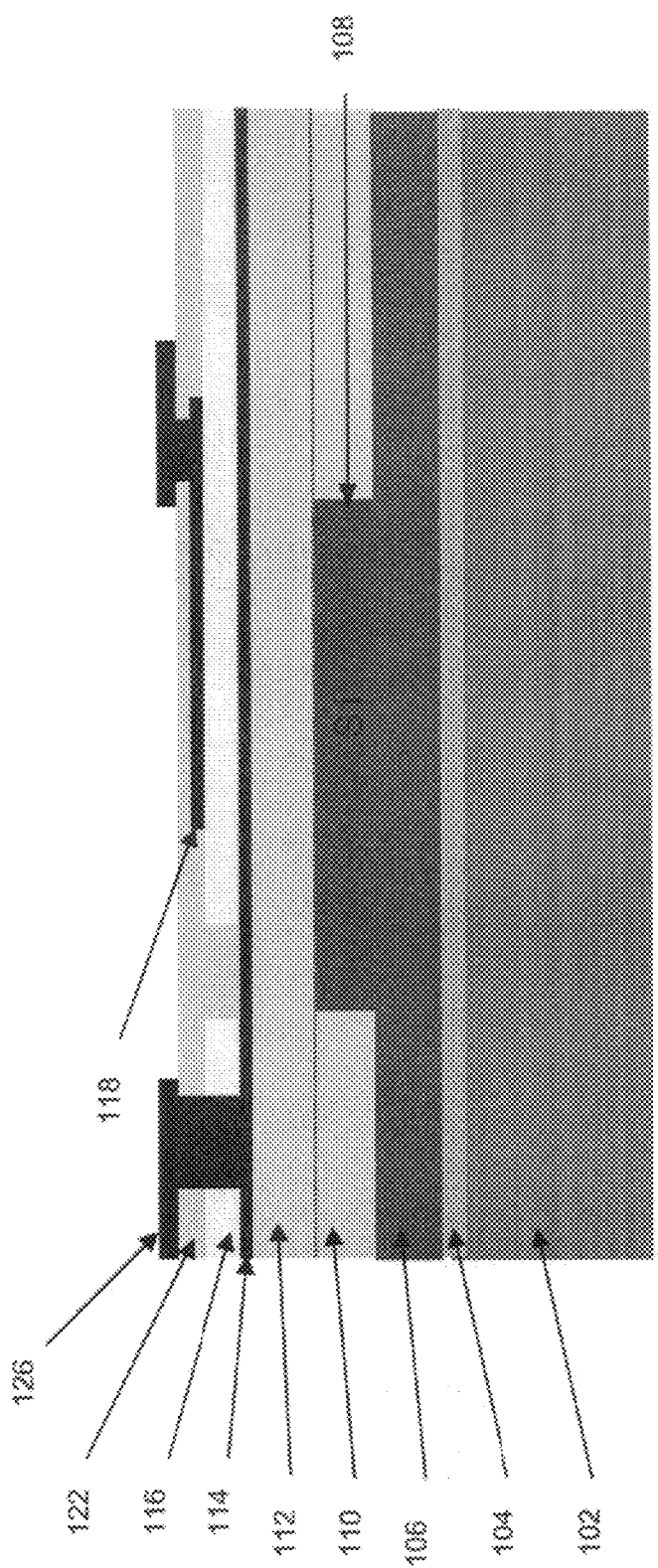

FIG. 1H illustrates an example of depositing a passivation layer (labeled as 122 and also referred to as ENC). FIG. 1I illustrates an example of opening and filling contact vias to create pads (labeled as 124 and also referred to as V2) at the top of the base polymer layer. FIG. 1J illustrates an example of forming a top redistribution layer (labeled as 126 and also referred to as M3) configured to route electrical signals to the first electrode and the second electrode.

FIGS. 2A-2D illustrate supplementary methods to the methods of FIGS. 1A-1J for forming a flexible PMUT array according to aspects of the present disclosure.

FIG. 2A illustrates an example of etching a release via (labelled as 202 and also referred to as V1), and removing sacrificial material to form a cavity through etching. FIG. 2B illustrates an example of forming the flexible PMUT array by releasing the carrier. According to aspects of the present disclosure, the PMUT as shown in FIG. 2B can be replicated to form a flexible PMUT array. In this particular implementation, the cavity of the PMUT may be opened on the front side of the PMUT. Vias and electrodes can be provided to allow the PMUT to be accessed and controlled through the redistribution layer or other means of routing.

FIG. 2C illustrates an example of laminating an encapsulation polymer (labeled 204 and also referred to as SE2) and patterning vias (labeled as 206 and also referred to as VP) for redistribution layer access. In some embodiments, when the cavity is encapsulated, the cavity may be a vacuum or partially pressurized by filling with a gaseous matter configured to achieve a desired frequency response.

FIG. 2D illustrates an example of forming the flexible PMUT array by releasing the carrier. According to aspects of the present disclosure, the PMUT as shown in FIG. 2D can be replicated to form a flexible PMUT array. In this particular implementation, the cavity of the PMUT may be concealed on the front side of the PMUT. Vias and electrodes can be provided to allow the PMUT to be accessed and controlled through the redistribution layer or other means of routing.

FIGS. 3A-3D illustrate supplementary methods to the methods of FIGS. 1A-1J for forming another flexible PMUT array according to aspects of the present disclosure.

FIG. 3A illustrates an example of laminating an encapsulation polymer configured to protect the PMUT and forming pattern vias 206 configured to support signal access through the redistribution layer. FIG. 3B illustrates a method of removing the release layer using a laser and separating the PMUT from the carrier. FIG. 3C illustrates an example of drilling a release via 302 in the first polymer layer 106, and forming a cavity 304 of the PMUT by removing the sacrificial material using the release via 302. According to aspects of the present disclosure, the PMUT as shown in FIG. 3C can be replicated to form a flexible PMUT array. In this particular implementation, the cavity 304 of the PMUT may be opened on the back side of the PMUT. Vias and electrodes can be provided to allow the PMUT to be accessed and controlled through the redistribution layer or other means of routing.

FIG. 3D illustrates an example of closing the cavity of FIG. 3C with an encapsulation polymer (labeled as 304 and also referred to as SE4). In some embodiments, when the cavity is encapsulated, the cavity may be a vacuum or partially pressurized by filling with a gaseous matter configured to achieve a desired frequency response.

FIGS. 4A-4F illustrate supplementary methods to the methods of FIGS. 1A-1J for forming yet another flexible PMUT array according to aspects of the present disclosure.

FIG. 4A illustrates an example of laminating a passivation polymer configured to encapsulate the first electrode, the piezoelectric layer and the second electrode, and patterning contact vias (labeled as 402 and also referred to as V2) configured to access the first electrode and the second electrode. FIG. 4B illustrates an example of depositing pads and/or a redistribution layer configured to route electrical signals to the first electrode and the second electrode.

Figure 4C:
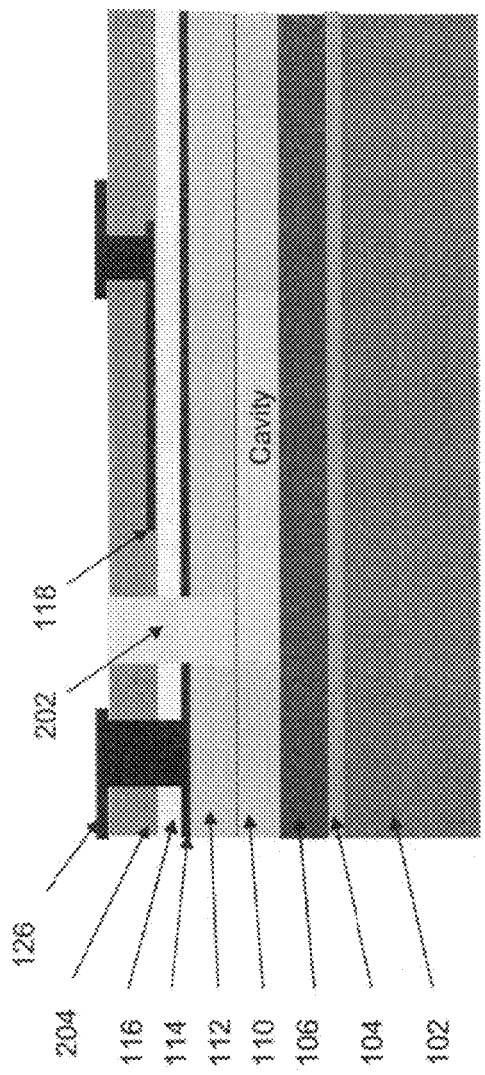
Figure 4D:
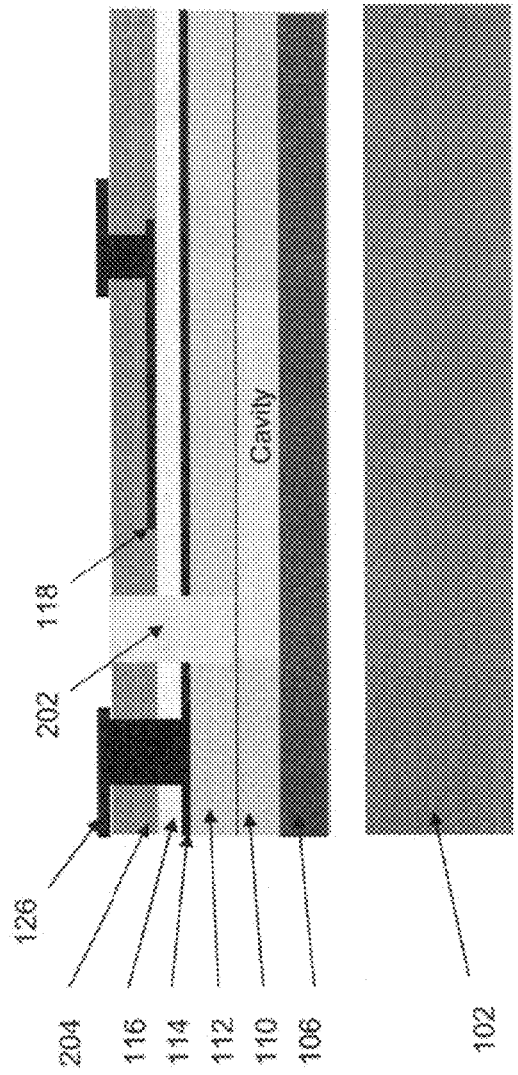

FIG. 4C illustrates an example of forming a cavity through a release via 202. FIG. 4D illustrates an example of removing the release layer to separate the PMUT from the carrier. According to aspects of the present disclosure, the PMUT as shown in FIG. 4D can be replicated to form a flexible PMUT array. In this particular implementation, the cavity of the PMUT may be opened on the front side of the PMUT. Vias and electrodes can be provided to allow the PMUT to be accessed and controlled through the redistribution layer or other means of routing.

FIG. 4E illustrates an example of laminating a passivation polymer (labeled as 404 and also referred to as SE3) to seal the release via 202, and patterning pad vias 206 configured to access the first electrode and the second electrode. In some embodiments, when the cavity is encapsulated, the cavity may be a vacuum or partially pressurized by filling with a gaseous matter configured to achieve a desired frequency response.

FIG. 4F illustrates an example of removing the release layer to separate the PMUT from the carrier. According to aspects of the present disclosure, the PMUT as shown in FIG. 4F can be replicated to form a flexible PMUT array. In this particular implementation, the cavity of the PMUT may be concealed on the front side of the PMUT. Vias and electrodes can be provided to allow the PMUT to be accessed and controlled through the redistribution layer or other means of routing.

FIGS. 5A-5D illustrate supplementary methods to the methods of FIGS. 1A-1J and FIGS. 4A-4B for forming yet another flexible PMUT array according to aspects of the present disclosure.

Figure 5C:
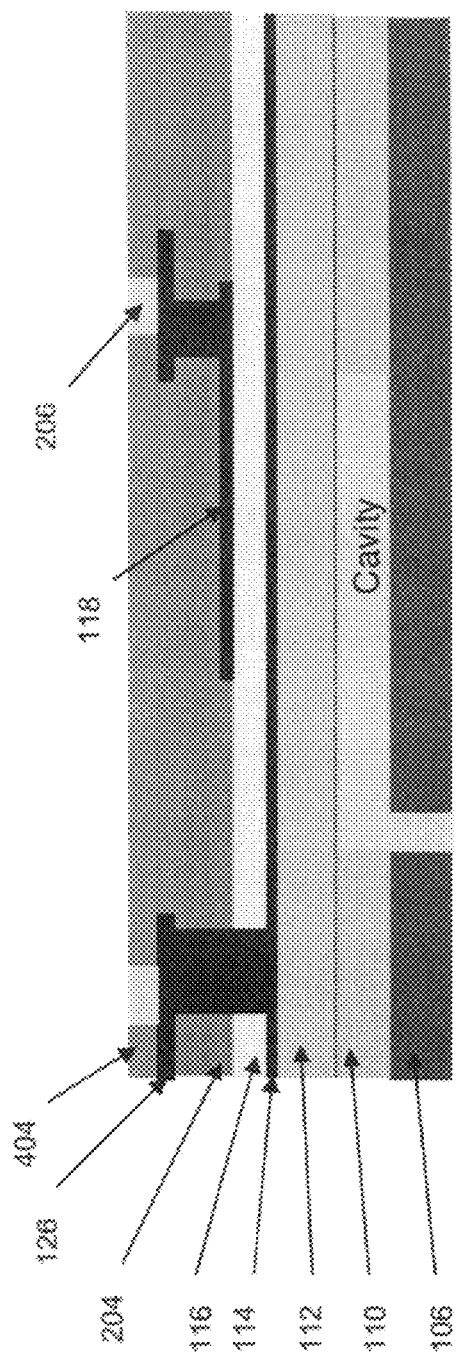

FIG. 5A illustrates an example of laminating a passivation polymer, and patterning pad vias 206 configured to access the first electrode and the second electrode. FIG. 5B illustrates an example of removing the release layer to separate the PMUT from the carrier. FIG. 5C illustrates an example of drilling a release via in the first polymer layer, and forming a cavity configured to adjust a frequency response of the PMUT by removing the sacrificial material using the release via. According to aspects of the present disclosure, the PMUT as shown in FIG. 5C can be replicated to form a flexible PMUT array. In this particular implementation, the cavity of the PMUT may be opened on the back side of the PMUT. Vias and electrodes can be provided to allow the PMUT to be accessed and controlled through the redistribution layer or other means of routing.

Figure 5D:
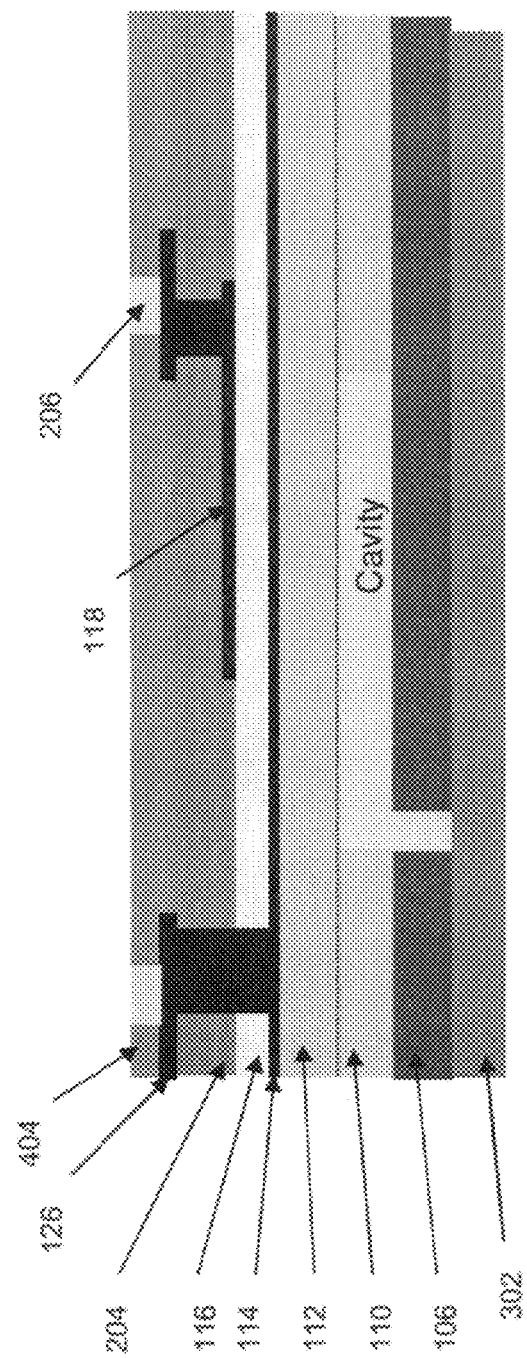

FIG. 5D illustrates an example of closing the cavity of FIG. 5C with an encapsulation polymer. In some embodiments, when the cavity is encapsulated, the cavity may be a vacuum or partially pressurized by filling with a gaseous matter configured to achieve a desired frequency response.

FIGS. 6A-6C illustrate an exemplary alternative implementation for forming a redistribution layer based on the methods shown in FIGS. 1A-1J through FIGS. 3A-3D.

FIG. 6A illustrates an example of etching contact vias configured to access the first electrode and the second electrode. FIG. 6B illustrates an example of depositing copper seed layer (labeled as 602 and also referred to as Seed) and patterning resist (labeled as 604 and also referred to as Resist). FIG. 6C illustrates an example of plating copper strip resist 604 and etching the copper seed layer.

FIGS. 7A-7D illustrate an exemplary alternative implementation for forming a redistribution layer based on the methods shown in FIGS. 1A-1J, FIGS. 4A-4F, and FIGS. 5A-5D.

FIG. 7A illustrates an example of laminating a passivation polymer layer and patterning contact vias. FIG. 7B illustrates an example of depositing copper seed layer and patterning resist. FIG. 7C illustrates an example of plating copper strip resist. FIG. 7D illustrates an example of etching the copper seed layer.

FIGS. 8A-8B illustrate an exemplary implementation for forming a cavity in a PMUT based on the methods shown in FIGS. 1A-1J through FIGS. 5A-5D. FIG. 8A illustrates an example of spinning on or blading thin sacrificial polymer layer. The material deposited in FIG. 8A can be a layer of polymer—laminated, spin on or doctor blade. The exposed sections may become PL1 in the methods described in FIGS. 1A-1J. It may then be exposed using a photo mask to define areas to either remove or leave behind. After exposure, the method may not perform a develop step but rather deposit the mechanical layer (polymer or oxide) and may continue as normal to make the PMUT. At the release steps, the method may release using liquid developer rather than gaseous chemistry as described above. For example, FIGS. 4C-4D illustrate an example of forming a cavity through a release from the top side of the PMUT, and FIGS. 5C-5D illustrate an example of forming a cavity through a release from the back side of the PMUT. FIG. 8B illustrates an example of depositing an oxide mechanical layer. Then, the methods as described in FIGS. 1A-1J through FIGS. 5A-5D may be carried out to the release etch steps.

According to aspects of the present disclosure, the flexible PMUT array may be used to form implantable/ingestible/wearable sensor devices. In some implementations, a flexible PC board may be bonded to the flexible PMUT array (FPA) using anisotropic conductive film (ACF), solder paste, or other methods. If a surface mount battery is not used, connect leads of external battery may be soldered to the flexible PC board. The flexible PC board and the FPA may be rolled around a cylindrical holder (or battery), and the components may be clamped/tacked together into a coiled assembly. Inside of the capsule may be coated with a thin layer of coupling material (such as polyimide or similar) and the coupling material may be partially cured (with UV or thermal). The coiled assembly may be inserted into the capsule (which has at least one end open) and then the coiled assembly may be released inside the capsule. Thereafter, the capsule may be filled with a coupling material or molding material and may be cured completely (for example, using 150 degrees C. snap cure or UV safe for insert assembly). Last but not least, open end(s) of the capsule may be sealed (or molded) using heat, adhesives or various sealing methods depending on materials choices. Note that local heating may be controlled in such a way that the inserted assembly would not be damaged in the sealing step.

The methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices designed to perform the functions described herein, or combinations thereof.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Wireless communication techniques described herein may be in connection with various wireless communications networks such as a wireless wide area network ("WWAN"), a wireless local area network ("WLAN"), a wireless personal area network (WPAN), and so on. The term "network" and "system" may be used interchangeably herein. A WWAN may be a Code Division Multiple Access ("CDMA") network, a Time Division Multiple Access ("TDMA") network, a Frequency Division Multiple Access ("FDMA") network, an Orthogonal Frequency Division Multiple Access ("OFDMA") network, a Single-Carrier Frequency Division Multiple Access ("SC-FDMA") network, or any combination of the above networks, and so on. A CDMA network may implement one or more radio access technologies ("RATs") such as cdma2000, Wideband-CDMA ("W-CDMA"), to name just a few radio technologies. Here, cdma2000 may include technologies implemented according to IS-95, IS-2000, and IS-856 standards. A TDMA network may implement Global System for Mobile Communications ("GSM"), Digital Advanced Mobile Phone System ("D-AMPS"), or some other RAT. GSM and W-CDMA are described in documents from a consortium named "3rd Generation Partnership Project" ("3GPP"). Cdma2000 is described in documents from a consortium named "3rd Generation Partnership Project 2" ("3GPP2"). 3GPP and 3GPP2 documents are publicly available. 4G Long Term Evolution ("LTE") communications networks may also be implemented in accordance with claimed subject matter, in an aspect. A WLAN may comprise an IEEE 802.11x network, and a WPAN may comprise a Bluetooth® network, an IEEE 802.15x, for example. Wireless communication implementations described herein may also be used in connection with any combination of WWAN, WLAN or WPAN.

In another aspect, as previously mentioned, a wireless transmitter or access point may comprise a femtocell, utilized to extend cellular telephone service into a business or home. In such an implementation, one or more mobile devices may communicate with a femtocell via a code division multiple access ("CDMA") cellular communication protocol, for example, and the femtocell may provide the mobile device access to a larger cellular telecommunication network by way of another broadband network such as the Internet.

Techniques described herein may be used with a GPS that includes any one of several GNSS and/or combinations of GNSS. Furthermore, such techniques may be used with positioning systems that utilize terrestrial transmitters acting as "pseudolites", or a combination of satellite vehicles (SVs) and such terrestrial transmitters. Terrestrial transmitters may, for example, include ground-based transmitters that broadcast a PN code or other ranging code (e.g., similar to a GPS or CDMA cellular signal). Such a transmitter may be assigned a unique PN code so as to permit identification by a remote receiver. Terrestrial transmitters may be useful, for example, to augment a GPS in situations where GPS signals from an orbiting SV might be unavailable, such as in tunnels, mines, buildings, urban canyons or other enclosed areas. Another implementation of pseudolites is known as radio-beacons. The term "SV", as used herein, is intended to include terrestrial transmitters acting as pseudolites, equivalents of pseudolites, and possibly others. The terms "GPS signals" and/or "SV signals", as used herein, is intended to include GPS-like signals from terrestrial transmitters, including terrestrial transmitters acting as pseudolites or equivalents of pseudolites.

The terms, "and," and "or" as used herein may include a variety of meanings that will depend at least in part upon the context in which it is used. Typically, "or" if used to associate a list, such as A, B or C, is intended to mean A, B, and C, here used in the inclusive sense, as well as A, B or C, here used in the exclusive sense. Reference throughout this specification to "one example" or "an example" means that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may comprise electronic signals, optical signals, electromagnetic signals, or any form of energy that provides information between locations.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of the appended claims, and equivalents thereof.

We claim:

1. A method of forming a flexible array of piezoelectric micromechanical ultrasonic transducers, comprising:
   providing a carrier configured to support the flexible array of piezoelectric micromechanical ultrasonic transducers (PMUTs);
   providing a release layer configured to adhere the flexible array of PMUTs to the carrier;
   forming the flexible array of PMUTs over the release layer, comprising
      for each PMUT in the flexible array of PMUTs,
      laminating a first polymer layer configured to support the PMUT;
      depositing a sacrificial material configured to pattern a cavity of the PMUT;
      depositing a mechanical layer, wherein the mechanical layer includes a planarization layer configured to provide chemical mechanical planarization to the PMUT, or a mechanical membrane configured to provide stiffness to the PMUT and frequency response adjustment;

depositing a first electrode configured to be coupled to a circuit ground plane;

depositing a piezoelectric layer configured to separate the first electrode and a second electrode;

depositing the second electrode configured to be coupled to a signal; and creating patterns on the first electrode, the piezoelectric material, and the second electrode configured to route control signals of the PMUT; and removing the release layer to separate the flexible array of PMUTs from the carrier.

2. The method of claim 1, further comprising:

depositing a passivation layer configured to encapsulate the first electrode, the piezoelectric layer and the second electrode;

etching contact vias configured to access the first electrode and the second electrode; and depositing pads and/or a redistribution layer configured to route electrical signals to the first electrode and the second electrode.

3. The method of claim 2, further comprising:

forming the cavity configured to adjust a frequency response of the PMUT.

4. The method of claim 3, further comprising:

laminating a second polymer layer configured to encapsulate the first electrode, the piezoelectric layer and the second electrode; and forming pattern vias configured to support signal access through the redistribution layer.

5. The method of claim 2, further comprising:

laminating a second polymer layer configured to encapsulate the first electrode, the piezoelectric layer and the second electrode;

forming pattern vias configured to support signal access through the redistribution layer; and separating the PMUT from the carrier.

6. The method of claim 5, further comprising:

drilling a release via in the first polymer layer; and forming the cavity configured to adjust a frequency response of the PMUT by removing the sacrificial material using the release via.

7. The method of claim 6, further comprising:

laminating a fourth polymer layer configured to enclose the cavity.

8. The method of claim 2, further comprising:

laminating a second polymer layer configured to encapsulate the first electrode, the piezoelectric layer and the second electrode;

patterning contact vias configured to access the first electrode and the second electrode; and depositing pads and/or a redistribution layer configured to route electrical signals to the first electrode and the second electrode.

9. The method of claim 8, further comprising:

forming the cavity configured to adjust a frequency response of the PMUT.

10. The method of claim 8, further comprising:

laminating a third polymer layer configured to protect the PMUT;

forming pattern vias configured to support signal access through the redistribution layer;

separating the PMUT from the carrier;

drilling a release via in the first polymer layer; and forming the cavity configured to adjust a frequency response of the PMUT by removing the sacrificial material using the release via.

11. The method of claim 10, further comprising:

laminating a fourth polymer layer configured to enclose the cavity.

12. The method of claim 9, further comprising:

laminating a third polymer layer configured to protect the PMUT; and forming pattern vias configured to support signal access through the redistribution layer.

* * * * *